United States Patent [19]

Koh et al.

[11] 4,094,650
[45] June 13, 1978

[54] INTEGRATED CATALYTIC GASIFICATION PROCESS

[75] Inventors: Kwang K. Koh, West Bloomfield, Mich.; Nicholas C. Nahas, Morris Plains, N.J.; Robert E. Pennington; Lonnie W. Vernon, both of Baytown, Tex.

[73] Assignee: Exxon Research & Engineering Co., Linden, N.J.

[21] Appl. No.: 740,987

[22] Filed: Nov. 11, 1976

Related U.S. Application Data

[63] Continuation-in-part of Ser. No. 514,852, Oct. 15, 1974, abandoned, which is a continuation-in-part of Ser. No. 287,319, Sep. 8, 1972, abandoned.

[51] Int. Cl.$^2$ .................... C10J 3/54; C10G 13/30
[52] U.S. Cl. .................... 48/197 R; 48/202; 48/213; 48/214 A
[58] Field of Search ............ 48/197 R, 196 R, 202, 48/204, 206, 207, 208, 210, 211, 214, 213; 423/205 (U.S. only)

[56] References Cited

U.S. PATENT DOCUMENTS

| 3,004,839 | 10/1961 | Tornquist | 48/197 R |
| 3,689,240 | 9/1972 | Aldridge et al. | 48/202 |
| 3,929,431 | 12/1975 | Koh et al. | 48/197 R |
| 3,975,168 | 8/1976 | Gorbaty | 48/197 R |
| 3,985,519 | 10/1976 | Kalina et al. | 48/210 |
| 3,998,607 | 12/1976 | Wesselhoft et al. | 48/197 R |

OTHER PUBLICATIONS

"Process for Coal Hydrogasification", C. G. von Fredersdorff Industrial and Engineering Chemistry, vol. 52, No. 7, Jul. 1960.

*Primary Examiner*—Richard V. Fisher
*Assistant Examiner*—Peter F. Kratz
*Attorney, Agent, or Firm*—James E. Reed; Yale S. Finkle

[57] ABSTRACT

Methane and carbon dioxide are produced by reacting steam with a carbonaceous feed material at a reaction temperature between about 1000° F. and about 1500° F. and a reaction pressure in excess of about 100 psia in the presence of a carbon-alkali metal catalyst and equilibrium quantities of added hydrogen and carbon monoxide. The raw product gas withdrawn from the reaction zone is treated for removal of the carbon dioxide, product methane is recovered from the treated gas, and the remaining hydrogen and carbon monoxide can be recycled to supply the added hydrogen and carbon monoxide needed in the reaction zone.

19 Claims, 1 Drawing Figure

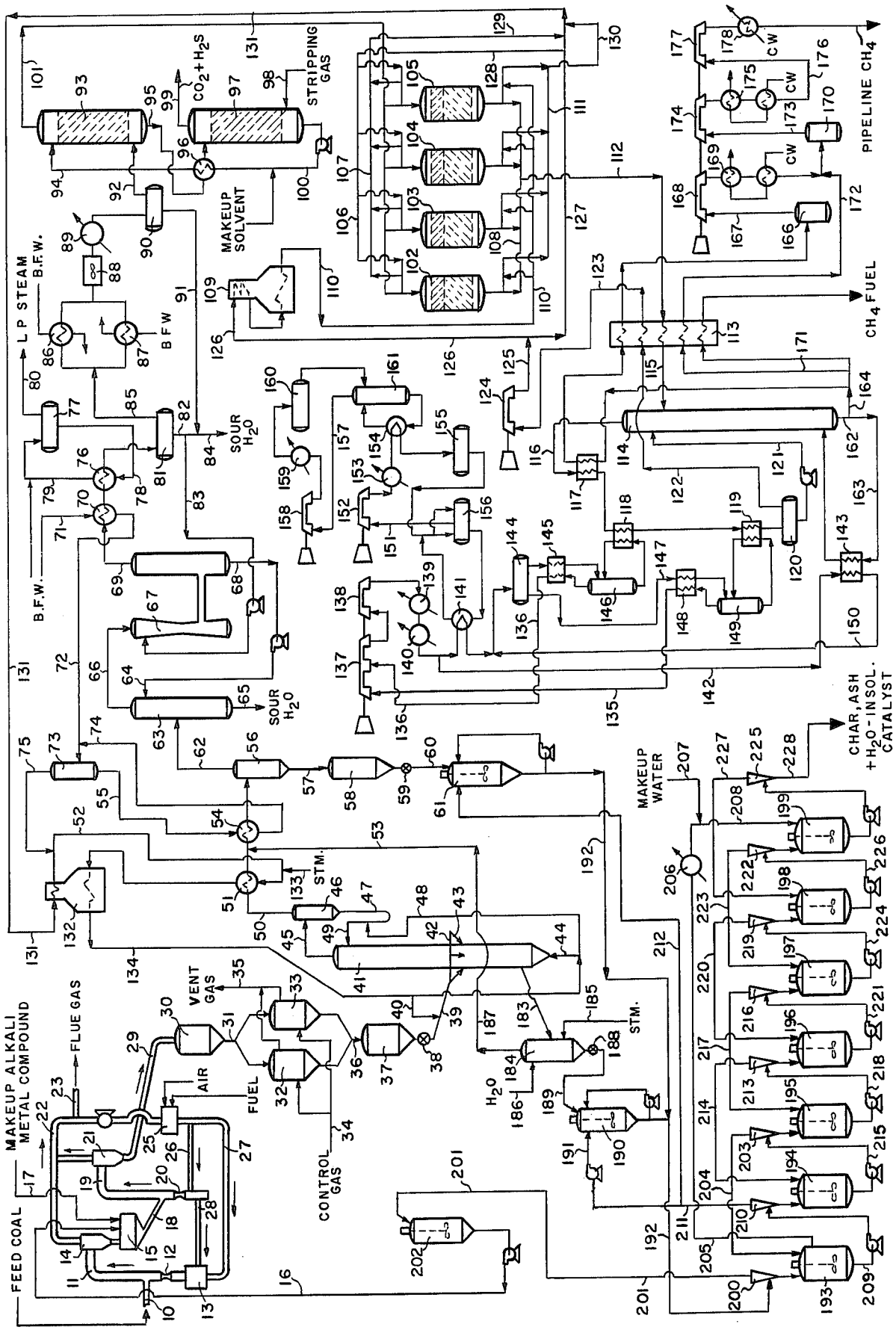

INTEGRATED CATALYTIC GASIFICATION PROCESS

CROSS-REFERENCE TO RELATED APPLICATIONS

This application is a continuation-in-part of application Ser. No. 514,852, filed in the United States Patent and Trademark Office on Oct. 15, 1974, which is a continuation-in-part of application Ser. No. 287,319, filed in the United States Patent and Trademark Office on Sept. 8, 1972 and both now abandoned.

BACKGROUND OF THE INVENTION

1. Field of the Invention

This invention relates to the gasification of coal and similar carbonaceous feed materials to produce methane and is particularly concerned with a catalytic gasification process carried out in the presence of a carbon-alkali metal catalyst.

2. Description of the Prior Art

Conventional processes for the manufacture of synthetic fuels by the gasification of coal or other carbonaceous solids generally require the reaction of carbon with steam, alone or in combination with oxygen, at temperatures between about 1200° and about 2500° F. to produce a gas which may contain some methane but consists primarily of hydrogen and carbon monoxide. This gas is subsequently reacted with additional steam to increase the hydrogen-to-carbon monoxide ratio by means of the water-gas shift reaction. Following this, the gas is usually treated to remove carbon dioxide and sulfur compounds and then fed to a catalytic methanation unit for reaction of the carbon monoxide and hydrogen to produce methane and water. It has been shown that processes of this type can be improved by carrying out the initial gasification step in the presence of a catalyst containing an alkali metal constituent. The alkali metal accelerates the steam-carbon gasification reaction and thus permits the generation of synthesis gas at somewhat lower temperatures than would otherwise be required or alternatively permits the use of a smaller reactor than might be necessary in the absence of such a catalyst. It is also known to carry out the water-gas shift reaction in the presence of such a catalyst.

The methanation reaction is conventionally carried out in the presence of a catalyst containing iron, nickel or cobalt as the principal constituent. Although catalysts of this type are reasonably effective, experience has shown that most such catalysts are highly sensitive to sulfur compounds and are quickly poisoned. To avoid this, the synthesis gas fed to the methanation unit may be treated to remove organic and inorganic constituents containing sulfur. This is generally done by first scrubbing the gas stream with a solvent such as monoethanolamine to eliminate most of the hydrogen sulfide, mercaptans, and the like and then removing the last traces of these impurities by adsorption on reduced zinc oxide or a similar adsorbent. Periodic regeneration of the methanation catalyst by treatment with hydrogen is generally required. These gas feed purification and catalyst regeneration steps are expensive. Moreover, the overall program is costly because of the large quantities of heat required in order to sustain the steam-carbon reaction, the large losses of low level exothermic heat of reaction from the water-gas shift and methanation reactions, and the substantial investment in equipment necessary to carry out the individual steps of the process.

To avoid difficulties of the type described above, it has been proposed that the steam-carbon reaction be used for the generation of a synthesis gas containing hydrogen and that the water-gas shift and methanation steps be eliminated by reacting the hydrogen thus produced with elemental carbon to form methane. It is known that the gasification of carbon with steam is an endothermic reaction and that the hydrogenation of carbon to form methane is exothermic. The heat liberated by the exothermic reaction of hydrogen with carbon to produce one mole of methane is about 83% of that necessary to generate the corresponding quantity of hydrogen by the endothermic reaction of steam with carbon. It has therefore been suggested that these two reactions be integrated to obtain an overall process which can be represented by the following equations:

$$C + 2H_2O \rightarrow 2H_2 + CO_2 + 39{,}000 \text{ Btu} \quad (1)$$

$$C + 2H_2 \rightarrow CH_4 + 32{,}570 \text{ Btu} \quad (2)$$

$$2C + 2H_2O \rightarrow CO_2 + CH_4 - 6570 \text{ Btu} \quad (3)$$

It has been proposed that these reactions be carried out simultaneously in parallel fluidized bed reaction zones. Ine one such reaction zone, feed coal would be reacted with recycle hydrogen at a pressure of 40 atmospheres and a temperature of 1500° F. or higher to produce methane. In the other such vessel, char withdrawn from the hydrogenation zone would be reacted with steam at 40 atmospheres and 1200° F. or higher to produce hydrogen and carbon dioxide. The gases from the hydrogenation zone would be treated for the recovery of methane and the remaining hydrogen would be recycled to the hydrogenation zone. Similarly, the gases from the steam gasification zone would be treated to remove carbon dioxide and the remaining hydrogen would be recycled to the hydrogenation zone. It has been said that the use of sodium carbonate as a catalyst in such a system is effective for the steam gasification reaction and will also help to increase the formation of methane in the hydrogenation reaction. The additional heat required to balance the system would be supplied by injecting oxygen into the steam gasification zone with the steam.

It has been said that a process of the type described above might conceivably be carried out in a single reaction vessel by introducing steam and recycle hydrogen into the vessel alternately. In an operation of this type, the injection of hydrogen would be commenced at a bed temperature of about 1500° F. and continued until the carbon temperature reached about 1700° F. At this point, the injection of hydrogen would be terminated and steam would be injected until the bed temperature had decreased from 1700° F. to about 1500° F. Temperatures of 1500° F. or higher are apparently required to achieve satisfactory carbon-hydrogen reaction rates. Again, tonnage oxygen would be added to the injected steam to burn carbon and supply the added heat necessary to balance the system. It has also been suggested that such a process might be carried out by mixing the steam and recycle hydrogen in related proportions and injecting them into the bed at temperatures between 1500° F. and 1700° F. so that the reaction of steam with carbon to produce hydrogen and the reaction of hydrogen with carbon to produce methane could take place simultaneously. Four moles of hydrogen would be recycled for each mole of methane produced and tonnage oxygen would be supplied to provide the necessary heat.

Noncatalytic processes which seek to integrate the steam-carbon and carbon-hydrogen reactions in a manner similar to that described above have been studied extensively. It has been stated in the literature that such a process would become increasingly endothermic as the reaction temperature increases and less endothermic with increases in the hydrogen-to-steam ratio in the gasifier. At high hydrogen-to-steam ratios, the process would allegedly approach thermal balance but require that substantial quantities of excess hydrogen be supplied from an external source. At low hydrogen-to-steam ratios, it has been said that sufficient hydrogen to satisfy the hydrogen requirements might be produced but that large amounts of heat would have to be supplied to this system. This imbalance between thermal and hydrogen requirements has been said to prevail at all possible gasification temperatures, even in those cases where the amount of available hydrogen is increased by including a water-gas shift step downstream of the gasifier.

It has been said that a process of the type referred to above would be thermodynamically feasible if operated at a temperature between about 1700° and 1800° F. and at a pressure of about 200 atmospheres and at a relatively low hydrogen-to-steam ratio so that sufficient hydrogen to keep the system in hydrogen balance would be produced and that the heat deficiency could be made up by preheating the reactants to high temperatures, by providing internal heat exchange with a high temperature fluid, or by partial combustion of coal within the gasifier. The first two alternatives would appear to be of questionable practicality because of the large amount of heat that would have to be supplied and the need for rapid heat transfer to make the furnishing of this heat feasible. The injection of oxygen into the gasifier would permit the generation of heat at the point where it is needed, alleviate the heat transfer problem, and at the same time provide a high temperature zone in which part of the inlet steam could be rapidly decomposed to obtain higher steam conversion rates than might otherwise be achieved. The use of oxygen in this manner would have disadvantages, however, because it could add significantly to the cost of the process, make operation of the gasifier more difficult, and reduce the overall process efficiency.

Although a process of the type outlined above would, if feasible, have pronounced advantages over conventional processes requiring separate shifting and downstream methanation of the raw product gas, studies have shown that there are serious problems associated with any such process. The analyses of such processes have assumed, for example, that the carbon-hydrogen reaction is in equilibrium but it can be shown that such will not be the case in a practical system. Published data on the relative rates of various reactions in a noncatalytic steam-carbon-hydrogen system have shown that this reaction proceeds at only about one-thousandth of the rate of the steam-carbon reaction. Moreover, it has been pointed out that an effective system of this type would require the use of two separate vessels, one for the hydrogenation reaction and a second immediately below the first for gasification of the residual carbon with steam and oxygen. As a result of these and other difficulties, it has been concluded in the literature that present-day gasification technology is inadequate to permit the conversion of steam and coal into methane and carbon dioxide in a single step and that a reaction sequence involving (1) steam gasification and the combustion of coal with oxygen as an initial step, (2) the water-gas shift reaction as an intermediate step, and (3) the downstream methanation of carbon monoxide as a final step must be employed.

SUMMARY OF THE INVENTION

This invention provides a substantially thermoneutral, hydrogen-balanced process for the generation of methane by the reaction of steam with coal, petroleum coke, heavy oil and other carbonaceous feed materials in the presence of recycle hydrogen and carbon monoxide which largely avoids the difficulties outlined above and has pronounced advantages over processes suggested in the past. In accordance with the invention, it has now been found that methane gas of essentially pipeline quality can be generated by reacting steam with a carbonaceous feed material in the presence of a carbon-alkali metal catalyst and equilibrium quantities of added hydrogen and carbon monoxide at a temperature between about 1000° and 1500° F. and a pressure in excess of about 100 psia, preferably between about 300 and about 1500 psia. The resulting raw product gas, an equilibrium mixture at reaction temperature, is withdrawn from the gasification zone, carbon dioxide is removed, and methane is recovered from the gas stream. The remaining hydrogen and carbon monoxide, present in the raw gas in equilibrium concentrations, can be recycled to the catalytic gasification zone to supply the added hydrogen and monoxide required. Alternatively, hydrogen and carbon monoxide derived from another source could be injected into the gasification zone to supply the added gases needed. Under these reaction conditions, the endothermic reaction of steam with carbon to form hydrogen and carbon monoxide, the exothermic reaction of carbon monoxide and steam to produce carbon dioxide and additional hydrogen, and the exothermic reaction of carbon monoxide with hydrogen to form methane and steam all take place simultaneously. The resulting hydrogen-balanced, substantially thermoneutral reaction which thus occurs in the gasification zone can be represented in simplified form by the equations:

$$2C + 2H_2O \rightarrow 2CO + 2H_2 \tag{4}$$

$$CO + H_2O \rightarrow CO_2 + H_2 \tag{5}$$

$$CO + 3H_2 \rightarrow CH_4 + H_2O \tag{6}$$

$$2C + 2H_2O \rightarrow CH_4 + CO_2 \tag{7}$$

It will be noted that hydrogen is neither consumed nor produced in this overall system. Aside from the contaminants formed from sulfur and nitrogen in the coal, the reaction products are essentially methane and carbon dioxide.

The process of the invention is based upon the discovery that catalysts produced by the reaction of carbon and alkali metal compounds such as potassium carbonate to form interlamellar carbon-alkali metal compounds or complexes will under the proper reaction conditions equilibrate the gas phase reactions occurring during gasification to produce additional methane and at the same time supply substantial amounts of additional exothermic heat in situ. This additional exothermic heat of reaction essentially balances the overall endothermicity of the reactions involving solid carbon and the water-gas shift reaction and thus results in a substantially thermoneutral process. This catalytic effect, not recognized in the past, also makes possible the production of essentially methane and carbon dioxide.

The gasification of coal and similar materials normally produces a synthesis gas composed primarily of hydrogen and carbon monoxide. The principal reactions which take place in such a system include the following:

$$C + H_2O \rightarrow CO + H_2 \text{ (Endothermic)} \qquad (8)$$

$$C + 2H_2 \rightarrow CH_4 \text{ (Exothermic)} \qquad (9)$$

$$C + CO_2 \rightarrow 2CO \text{ (Endothermic)} \qquad (10)$$

$$CO + H_2O \rightleftarrows CO_2 + H_2 \text{ (Exothermic)} \qquad (11)$$

The reaction kinetics during conventional gasification operations are such that the product gas normally contains only small amounts of methane at best. In steam gasification, the methane which is present occurs primarily as a result of devolatilization of the coal. The direct hydrogenation of carbon in accordance with equation (9) above is known to be very slow as compared to the endothermic reactions of steam and carbon dioxide with carbon as set forth in equations (8) and (10). The products of conventional steam gasification operations are thus primarily hydrogen and carbon monoxide and such operations are highly endothermic. As pointed out earlier, it has been proposed that this endothermicity be reduced by carrying out the operation in the presence of hydrogen to promote the exothermic carbon-hydrogen reaction of equation (9) but this normally requires a substantially higher reaction temperature than is needed for the steam-carbon reaction.

It has now been found that the carbon-alkali metal catalysts have a surprisingly potent catalytic effect on the gas phase reactions, as opposed to the solid-gas reactions, which allows the following exothermic reactions to contribute substantially to the presence of methane in the effluent gas and, more importantly, drastically reduces the endothermicity of the overall reaction:

$$2CO + 2H_2 \rightarrow CO_2 + CH_4 \text{ (Exothermic)} \qquad (12)$$

$$CO + 3H_2 \rightarrow H_2O + CH_4 \text{ (Exothermic)} \qquad (13)$$

$$CO_2 + 4H_2 \rightarrow 2H_2O + CH_4 \text{ (Exothermic)} \qquad (14)$$

Under the proper operating conditions, these reactions can be made to take place within the gasification zone and supply large amounts of methane and exothermic heat which would otherwise have to be supplied by the injection of oxygen or by other means. In the presence of a carbon-alkali metal catalyst and equilibrium amounts of added hydrogen and carbon monoxide at temperatures of about 1000° F. to about 1500° F. and pressures in excess of about 100 psia, preferably between about 300 and 1500 psia, the reactions involving elemental carbon proceed as indicated by equations (8), (9) and (10) above; the water-gas shift reaction shown by equation (11) may proceed in either direction depending upon the amount of steam and other materials present; and the catalyzed gas phase reactions (12), (13) and (14) result in the consumption of hydrogen and carbon oxides formed in the other reactions to produce additional methane, carbon dioxide and water and generate very substantial quantities of heat. Laboratory and pilot plant tests have shown that the constituents of the raw product gas are present in equilibrium concentrations at the reaction temperature. Ignoring contaminants formed as a result of the presence of sulfur and nitrogen in the coal or feed material, essentially only methane and carbon dioxide are produced. The overall reaction is substantially thermoneutral and requires only a very small heat input. The modest heat input needed can be readily supplied by preheating the reactants to temperatures easily handled with present day technology. Unlike earlier processes, the preheat temperatures needed are not so high that the injection of tonnage oxygen is the only viable way of supplying the required heat. If desired, oxygen can be introduced into the system to aid in raising the reactants to the reaction temperature and compensating for heat losses but this is not essential. The necessity for downstream shifting of the gas and the need for subsequent catalytic methanation are eliminated. As a result, the process has pronounced technical and economic advantages over those proposed heretofore.

The carbon-alkali metal catalyst employed in the process of the invention is prepared by heating an intimate mixture of carbon and an alkali metal constituent to an elevated temperature, preferably a temperature of about 800° F. or higher. The heating step can be carried out in a solid feed preparation zone, in an external heater, or within the gasifier used in the process of the invention. Carbonaceous solids which may be employed in preparing the catalysts include coal, coal char, metallurgical coke, petroleum coke, charcoal, activated carbon, and the like. In some cases inert carriers having carbon deposited on their outer surfaces can also be used. Suitable inert carriers include silica, alumina, silica-alumina, kieselguhr, naturally occurring zeolites, synthetic zeolites, spent cracking catalysts, and the like. The carbonaceous solids selected for use in the gasification of coal or other solid feed materials will in most instances be the carbonaceous feed solids which are to be gasified but in some variations of the process carbonaceous materials other than the feed solids may be used. The catalyst particles, whether composed substantially of carbon and an alkali metal constituent or made up of carbon and an alkali metal constituent deposited on an inert carrier, may range from fine powders to coarse lumps, particles between about 4 and about 100 mesh on the U.S. Sieve Series Scale generally being preferred. The size selected for use in a particular operation will normally depend in part on the gas velocities and other conditions within the system in which the catalyst is to be used. In fluidized bed systems, the particles size is in part dependent upon the conditions under which the bed is to be operated. In fixed or moving bed systems, the catalyst particle size is generally of less importance.

Any of a variety of alkali metal constituents can be used in preparing the carbon-alkali metal catalysts. Suitable constituents include the alkali metals themselves and alkali metal compounds such as the alkali metal carbonates, bicarbonates, formates, biphosphates, oxalates, aluminates, amides, hydroxides, acetates, sulfates, hydrosulfates, sulfides, tungstates and mixtures of these and similar compounds. All of these are not equally effective and hence catalysts prepared from certain alkali metal constituents can be expected to give somewhat better results under certain conditions than do others. In general, cesium, potassium, sodium and lithium salts derived from organic or inorganic acids having ionization constants less than about $1 \times 10^{-3}$ and alkali metal hydroxides are preferred. The cesium compounds are generally the most effective, followed by the potassium, sodium and lithium compounds in that order. Because of their high activity, relatively low cost compared to cesium compounds, and ready availability, potassium compounds or mixtures of potassium and sodium compounds are generally employed. Potassium carbonate or mixtures of potassium carbonate and sodium carbonate are especially effective.

Depending upon the particular material selected and the manner in which the process of the invention is to be carried out, the alkali metal constituent and carbonaceous solid can be combined to form an intimate mixture of the two in a variety of different ways. A generally preferred procedure is to dissolve a water-soluble alkali metal salt or hydroxide in an aqueous carrier, impregnate the carbonaceous solids with the resulting aqueous solution by soaking or spraying the solution onto the particles, and thereafter dry the solids. In some cases, however, the carbonaceous material can be impregnated by suspending a finely divided alkali metal or alkali metal compound in a hydrocarbon solvent or other inert liquid carrier of suitably low viscosity and high volatility and thereafter treating the solid with the liquid containing the alkali metal constituent. In other instanes, it may be advantageous to pelletize a very finely divided alkali metal or alkali metal compound with carbon and an oil or similar binder and then heat the pellets to an elevated temperature. Other catalyst preparation methods, including simply mixing finely divided carbonaceous material with a powdered alkali metal salt and thereafter heating the mixture to the desired temperature, can in some cases also be used. If an alkali metal per se is employed in the preparation step, suitable precautions against ignition of the alkali metal will have to be taken.

It is generally advantageous to combine the carbonaceous material with from about 5 to about 50 weight percent of the alkali metal constituent, preferably from about 10 to about 30 percent by weight, in preparing the catalyst. The optimum amount of the alkali metal constituent will depend in part upon the particular constituent and preparation method selected. If an impregnation process is to be used in preparing the catalyst, multiple impregnation and drying steps may be employed to achieve high alkali metal constituent-to-carbon ratios. The particles containing carbon and the alkali metal constituent can be heated to temperatures sufficiently high to produce a reaction between the two in an external furnace or the like. In the gasification of coal or other carbonaceous solids, however, it is generally preferred to prepare a suitably intimate mixture of the carbonaceous solids to be gasified and the alkali metal constituent to be used and then introduce this mixture into hot gasification equipment in which the catalyst is to be employed. As the particles are heated to the gasification temperature, the carbon and alkali metal constituent react to produce the catalyst. Externally prepared catalysts may be presulfided by exposing them to hydrogen sulfide before they are used if desired.

The mechanisms which take place as the result of combining the carbonaceous solids and alkali metal constituents and then heating them to elevated temperatures are not fully understood. Apparently the alkali metal reacts with the carbon to form interlamellar carbon-alkali metal compounds or complexes. Studies have shown that neither carbonaceous solids nor the alkali metal constituents alone are fully effective for establishing equilibrium conditions for gas phase reactions involving steam, hydrogen, carbon monoxide, carbon dioxide and methane and that catalytic activity is obtained only when a compound or complex of the carbon and alkali metal is present in the system. Both constituents of the catalyst are therefore necessary. Experience has shown that these catalysts are resistant to degradation in the presence of sulfur compounds, that they resist sintering at high temperatures, and that they bring gas phase reactions involving the gases normally produced during coal gasification into equilibrium. As a result of these and other beneficial properties, these catalysts have pronounced advantages over other catalysts employed in the past.

The temperature employed in carrying out the process of the invention will depend in part upon the particular feedstock and catalyst used, the reactor configuration employed, the system used to preheat the reactants to the reaction temperature, and other factors but will normally range between about 1000° and about 1500° F. At temperatures below about 1000° F., low reaction rates tend to limit the process. At temperatures above 1500° F., the yields of methane tend to be low, large volumes of gas must be handled per unit volume of methane recovered, and the process may tend to become thermally imbalanced. The use of a single or multistage fluidized bed system and reaction temperatures between about 1200° and about 1400° F. are generally preferred. Similarly, the reaction pressure will generally exceed 100 psia and will normally range between about 300 and about 1500 psia. At pressures below about 100 psia, the methane yields tend to be low. They increase rapidly between 100 and 500 psia. Above about 1500 psia the cost of the equipment required may not justify the use of higher pressures. Pressures between about 300 and about 1200 psia are particularly effective.

The process of the invention is carried out in the presence of equilibrium quantities of added hydrogen and carbon monoxide. The added gases will normally be obtained by removing carbon dioxide and hydrogen sulfide from the raw product gas, recovering methane from the treated gas cryogenically, and then recycling the remaining hydrogen and carbon monoxide to the gasification reactor. In lieu of this, however, it may in some cases be advantageous to supply the needed hydrogen and carbon monoxide from an external source and thus omit the recycling step. If gas from an external source is used, the hydrogen and carbon monoxide need not necessarily be present in the equilibrium ratio. If the required quantity of gas is present, the equilibrium ratio will be achieved within the gasifier as a result of the water-gas shift reaction. If hydrogen and carbon monoxide are available in quantities greater than the equilibrium amounts, excess quantities can be introduced to produce additional methane by the methanation reactions. If this is done, the system will tend to become exothermic and further heat economies are possible. In any case, the reaction of a carbonaceous feed material with steam in the presence of the catalyst and equilibrium quantities of added hydrogen and carbon monoxide under the temperature and pressure conditions specified permits conversion of the feed material into essentially methane and carbon dioxide without the necessity for separate downstream shifting and methanation steps, significantly reduces the cost of preparing pipeline quality gas from coal and other carbonaceous feed materials, permits economies in gasifier materials and construction, reduces heat transfer requirements between feed and product streams, simplifies the recovery of alkali metal constituents from spent catalyst, and has other pronounced advantages over gasification processes advocated in the past.

BRIEF DESCRIPTION OF THE DRAWING

The drawing is a schematic flow diagram illustrating a preferred process carried out in accordance with the invention for the manufacture of methane by the gasification of coal or similar carbonaceous solids in the presence of a carbon-alkali metal catalyst and recycle quantities of hydrogen and carbon monoxide.

DESCRIPTION OF THE PREFERRED EMBODIMENTS

In the preferred embodiment of the invention illustrated in the drawing, particles of bituminous coal, sub-bituminous coal, lignite or other carbonaceous solid feed material crushed to a particle size of about 8 mesh on the U.S. Sieve Series Scale or smaller is fed into the system through line 10 from a coal preparation plant or storage facility which does not appear in the drawing. The solid feed material may be introduced into the system in any of a variety of different ways. In the particular system shown, the feed coal is moved through line 10 and into the first stage 11 of the feed preparation system by means of a screw conveyor which is not shown. This first stage includes an entrainment dryer having an integral venturi classifier 12 and a gas-swept hammer mill crusher 13 near its lower end. The coal particles discharged into stage 11 are entrained in a stream of hot gas at a temperature of about 250° F. or higher moving upwardly through the system and carried overhead to first stage cyclone 14 where the partially dried particles are removed from the gas and discharged downwardly into a pug mill 15. In the first stage, the moisture content of the coal will be reduced to about 6% based on the weight of the wet coal. In the pug mill, the coal particles are mixed with a recycled solution of sodium carbonate and potassium carbonate supplied through line 16 and with makeup quantities of dry sodium carbonate and potassium carbonate introduced through line 17. The composition of the recycled solution of alkali metal constituents and the amount of dry makeup sodium carbonate and potassium carbonate required will depend to a large extent upon the operation of the catalyst recovery system to be described hereafter and may be varied as necessary. It is generally preferred to employ the sodium carbonate and potassium carbonate used for makeup purposes in approximately equal quantities. It will be understood, of course, that the invention is not restricted to the use of this particular mixture of alkali metal constituents and that other materials may be used. For purposes of illustrating the invention, it will be assumed that the feed coal is an Illinois No. 6 coal having the composition shown in Table I below and that the recycle solution of sodium carbonate and potassium carbonate and makeup sodium and potassium carbonate are added in amounts sufficient to provide 13 weight percent of a mixture of equal parts of sodium carbonate and potassium carbonate on a moisture-free basis.

TABLE I

| Coal Analysis | |
|---|---|
| Ultimate Analysis, Wt. % as Received | Values |
| Moisture | 16.50 |
| Carbon | 58.17 |
| Hydrogen | 4.22 |
| Oxygen | 7.89 |
| Nitrogen | 1.54 |
| Sulfur | 3.50 |
| Ash | 8.18 |
| Total | 100.00 |
| Higher Heating Value, Btu/lb. as Received | 10,630 |

The product from pug mill 15 is discharged through screw conveyor 18 into the second stage 19 of the apparatus. This second stage includes an entrainment dryer having a venturi classifier 20 near its lower end. Solids entering the second stage are entrained in hot gas moving upwardly through the entrainment dryer above the venturi classifier. Any oversize particles greater than about 8 mesh which may have been formed in the pug mill are not entrained and instead pass downwardly through the venturi classifier. Gases containing the entrained solids move upwardly through the entrainment dryer into cyclone 21 where the solids are separated from the gas. The overhead gases are combined with those from cyclone 14 and passed through line 22. A portion of this gas is discharged through line 23 to a bag house or other flue gas handling facilities and the remaining gas is passed by means of blower 24 to combustion chamber 25 where it is heated. A coal-fired combustion chamber will normally be employed but other systems may be used if desired. The hot gas, at a temperature of about 300° F. or higher, is passed in part through line 26 to the second stage of the system. The remaining hot gas passes through line 27 to hammer mill 13. Here the oversize particles removed in the second stage of the system and transported to the hammer mill by screw coveyor 28 are crushed to 8 mesh or smaller and carried upwardly into the first stage by the hot gas passing through the hammer mill. The solids removed from the gas leaving the second stage are withdrawn by means of a screw conveyor 29 and transported to a low pressure hopper 30. These solids, composed of feed coal impregnated with sodium carbonate and potassium carbonate, will contain about 3.5 weight percent moisture and will be at a temperature of about 200° F. On a dry basis, the coal will contain about 6.5 weight percent sodium carbonate and about 6.5 weight percent potassium carbonate.

The impregnated feed coal fed into low pressure hopper 30 as described above is passed through line 31 into one of two or more parallel lock hoppers 32 and 33. These lock hoppers are provided with gas lines 34 for the introduction of recycle hydrogen and carbon monoxide or other control gas separately into each hopper at a pressure sufficient to move the solid feed material into the gasifier and with vent lines 35 for separately exhausting high pressure gas from each hopper. The recycle hydrogen and carbon monoxide employed will, as pointed out hereafter, contain some methane not removed during the separation step of the process. The system will normally include means for recovering, scrubbing, storing and reusing the control gas which are not shown in the drawing and are unnecessary for an understanding of the invention. The pressure at which the lock hoppers are operated will depend primarily upon the gasification pressure. In the particular system shown, the gasifier is operated at a pressure of 500 pounds per square inch absolute and hence the lock hoppers will normally be operated at a pressure of about 750 psia. The hoppers are operated alternately, one being used for the transport of feed solids to the gasifier while the other is being filled with incoming feed solids from low pressure hopper 30. Solids from the lock hoppers are discharged through line 36 into high pressure feed hopper 37 and then passed through star wheel feeder or similar device 38 into feed line 39. Here a mixture of steam and recycle hydrogen and carbon monoxide introduced through line 40 is added to the feed stream in a quantity sufficient to give a solids-to-gas ratio between about 0.2 and about 5.0 pounds of solid feed material per actual cubic feet of gas including steam. In the particular system shown, the added steam and recycle hydrogen and carbon monoxide will be at a temperature of about 1450° F. and at a pressure of about 520 psia.

The feed stream prepared as described above is fed into gasifier 41 through fluid-cooled nozzles not shown in the drawing. The cooling fluid will normally be steam but other fluids can also be used. This fluid may be circulated within the nozzles for cooling purposes or injected into the gasifier around the feed stream to control entry of the solids into the fluidized bed within the gasifier. The system shown in the drawing includes a manifold 42 and four injection lines 43 extending into the vessel from the manifold at equally spaced intervals around the reactor periphery. The number of nozzles provided will depend primarily upon the size of the gasifier and the feed rate required and may be varied as desired.

The gasifier employed in the system shown in the drawing comprises a refractory-lined vessel containing a fluidized bed of carbonaceous solids and catalyst extending upwardly in the vessel above an internal grid or similar distribution device which is located near the lower end of the gasifier and does not appear in the drawing. The bed is maintained in the fluidized state by means of a mixture of steam and recycle hydrogen and carbon monoxide introduced below the grid or similar device through line 44. In the particular system shown, this mixture contains about 63.3 mole percent steam and about 36.7 mole percent of recycle gas containing about 21.0 mole percent of carbon monoxide, about 68.8 mole percent of hydrogen, and about 10.2 mole percent of methane. The space velocity of the upflowing stream within the fluidized bed will normally range between about 300 and about 3000 volumes of steam and recycle gas per volume of fluidized solids. In the system shown, about 0.09 mole of steam and recycle gas per pound of solids fed to the gasifier is used.

Within the fluidized bed in gasifier 41, the injected steam reacts with solid carbon in the feed material at a bed temperature of about 1300° F. and a pressure of about 500 psia. Due to the gas phase equilibrium conditions existing as a result of the carbon-alkali metal catalyst and due to the presence of equilibrium quantities of recycle hydrogen and carbon monoxide injected with the steam near the lower end of the bed, the reaction products will normally consist essentially of methane and carbon dioxide. Competing reactions which in the absence of the catalyst and the recycle gases would ordinarily tend to produce additional hydrogen and carbon monoxide are suppressed. At the same time, substantial quantities of exothermic heat are released as a result of the reaction of hydrogen with carbon oxides and the reaction of carbon monoxide with steam. This exothermic heat tends to balance the endothermic heat consumed by the reaction of steam with carbon. So far as the heat of reaction is concerned, the gasifier is therefore largely in heat balance. The heat employed to preheat the feed coal to the reaction temperature and compensate for heat losses from the gasifier is supplied for the most part by excess heat in the steam and recycle gas. In the absence of the exothermic heat provided by the catalyzed gas phase reactions, the steam and recycle gas would have to be heated to substantially higher temperatures than those employed here. As an alternate to the use of these higher temperatures, oxygen could be injected to supply the needed heat by combustion of a part of the carbon. In this process, the injection of oxygen is unnecessary. If desired, however, oxygen can be introduced to permit the use of even lower recycle gas and steam temperatures. It is generally preferred to avoid oxygen injection but there may be cases in which the introduction of small amounts of oxygen and reduction of the size of the furnace employed to preheat the recycle gas and steam will be economically advantageous.

The portion of the gasifier above the fluidized bed serves in part as a disengagement zone in which particles too heavy to be entrained by the gas leaving the vessel are returned to the fluidized bed. Although not shown in the drawing, the disengagement zone may include one or more cyclone separators or similar devices for removing relatively large particles from the gas. The gas passing upwardly from the fluidized bed through the disengagement zone and leaving the gasifier by means of line 45 will normally contain methane and carbon dioxide produced by the reaction of steam and carbon in the presence of the carbon-alkali metal catalyst, trace quantities of ethylene and other hydrocarbons, unreacted steam, hydrogen and carbon monoxide in quantities corresponding to those introduced with the recycle gas, hydrogen sulfide and ammonia present as the result of sulfur and nitrogen in the coal, trace quantities of other contaminants, and entrained fines. In the particular system shown, the gas composition is as follows:

TABLE II

| Raw Product Gas Composition | |
|---|---|
| Component | Mole % |
| CO | 7.1 |
| $CO_2$ | 14.3 |
| $H_2$ | 23.0 |
| $H_2O$ | 31.2 |
| $CH_4$ | 22.8 |
| $C_2H_6$ | Tr |
| $H_2S$ | 0.8 |
| $NH_3$ | 0.8 |

The gas leaving the gasifier through overhead line 45 is passed to primary cyclone separator 46 where the larger fines present in the gas stream are removed. These fines pass downwardly through dip leg 47, are entrained in a mixture of steam and recycle gas introduced through line 48, and are returned to the upper part of the gasifier through line 49. The overhead gas from the cyclone separator, at a temperature of about 1300° F. and a pressure of about 495 psia, is passed through line 50 to gas-gas heat exchanger 51 where it is cooled by indirect heat exchange with a mixture of recycle hydrogen and carbon monoxide and steam from line 52. This results in a drop in the temperature of the gas stream from about 1300° F. to about 866° F. Following this, the gas is further cooled by the introduction of steam from the char quench drum through line 53 and then cooled still further in exchanger 54 by indirect heat exchange with steam from line 55. The gas stream, now at a temperature of about 536° F. is then introduced into secondary cyclone separator 56 where additional entrained fines are removed from the gas. These fines pass downwardly through dip leg 57 into high pressure fines hopper 58. The particles are discharged from the hopper at a temperature of about 536° F. through fines feeder 59 and line 60 into agitated fines slurry drum 61 for subsequent recovery of alkali metal constituents from the fines as described hereafter.

The gas from which the fines have been removed is taken overhead from secondary cyclone 56 through line 62 and introduced into cyclonic scrubber 63 where it is contacted with water introduced through line 64 to cool the gas to a temperature of about 379° F. at a pressure of 482 psia and remove additional solids. The scrubber water is withdrawn through line 65 and passed to sour water treatment facilities not shown in the drawing. The gas taken overhead through line 66 passes to venturi scrubber 67 where it is further scrubbed and cooled to a slightly lower temperature. The water from the venturi scrubber passes through line 68 into line 64 and is reused in the cyclonic scrubber. The gas leaving the venturi scrubber through line 69 passes through boiler feed water heater 70 and gives up heat to water introduced through line 71. The heated water then passes through line 72 into high pressure steam drum 73, along with steam from exchanger 54 introduced through line 74. Condensate from the bottom of the steam drum is circulated to the exchanger through line 55. Steam is taken overhead from this drum at a temperature of about 486° F. through line 75 for use in the gasification step of the process.

The raw product gas passes from the boiler feed water heater to low pressure steam generator 76 where it gives up additional heat to water circulated from low pressure steam drum 77 through line 78. The resulting steam is returned to the drum through line 79 and low pressure steam is withdrawn from the drum through line 80. From the steam drum, the gas passes to primary product gas flash drum 81 where water is separated from the gas and withdrawn through line 82. A portion of this water is passed through line 83 for use in the venturi scrubber and the remaining water is discharged through line 84 to sour water treatment facilities not shown. The gas from the primary flash drum passes through line 85 and boiler feed water heaters 86 and 87 into product gas air cooler 88. From here it flows through product gas heat exchanger 89 where it is further cooled to a temperature of about 110° F. This relatively cool gas is then introduced into secondary product gas flash drum 90 at a pressure of about 460 psia. Water separated from the gas is passed through line 91 to sour water treatment facilities and the gas stream is introduced through line 92 into the acid gas removal section of the process.

In the acid gas removal unit, the gas introduced through line 92 is contacted in solvent scrubber 93 with a solvent such as monoethanolamine, diethanolamine, a solution of sodium salts of amino acids, methanol, hot potassium carbonate or the like introduced into the upper part of the vessel through line 94. Any of a variety of conventional solvent treating processes used for the removal of acidic constituents from gas streams may be employed. The spent solvent containing carbon dioxide, hydrogen sulfide and other contaminants removed from the gas is withdrawn from vessel 93 through line 95, passed in indirect heat exchange with the regenerated solvent in exchanger 96 and introduced into the upper part of regeneration vessel 97. Here the spent solvent is contacted with steam or other stripping gas introduced through line 98 and the stripping gas containing carbon dioxide and hydrogen sulfide removed from the solvent is taken off overhead through line 99. This gas stream can then be further treated for the recovery of sulfur by conventional means. The process employed will depend primarily upon the particular solvent utilized. The regenerated solvent is withdrawn from the bottom of the vessel 97 through line 100 and recirculated through heat exchanger 96 and line 94 to treating vessel 93. The clean product gas, at a temperature of about 95° F. and a pressure of about 435 psia, is taken overhead through line 101. The composition of this gas will be as follows:

TABLE III

| Clean Product Gas Composition | |
|---|---|
| Constituent | Mole % |
| CO | 13.4 |
| $CO_2$ | 0.1 |
| $H_2$ | 43.6 |
| $H_2O$ | 0.1 |
| $CH_4$ | 42.8 |

The clean gas from the acid gas removal unit is passed through line 101 to a molecular sieve adsorption unit for the removal of the remaining carbon dioxide and water. The unit shown includes four parallel adsorption vessels 102, 103, 104 and 105 containing a commercial molecular sieve on which the carbon dioxide and water are retained. Each adsorption vessel may contain a guard bed upstream of the sieve to prevent damage to the sieve material. The adsorption vessels are manifolded on the upstream side to permit the introduction of clean feed gas from line 101, the introduction of recycle gas from line 106, and the recovery of desorbed materials through line 107. On the downstream side, the desorption vessels are manifolded to permit the recovery through line 108 of product gas from which carbon dioxide and water vapor have been removed, the introduction of hot desorbing gas from furnace 109 through line 110, and the recovery through line 111 of desorbing gas which has been displaced by fresh feed gas from line 101. These vessels are operated in sequence, at least one vessel being used for the adsorption of carbon dioxide and water from the incoming feed gas while others are being desorbed and purged of the desorbing gas. The valving and control system employed for sequential operation of the sieve unit is not shown in the drawing and may be of conventional design.

The product gas from the molecular sieve unit, substantially free of carbon dioxide and water vapor and containing about 13.4% carbon monoxide, about 43.7% hydrogen, and about 42.9% methane, is passed through line 112 to methane recovery tower feed-product gas heat exchanger 113. Here the incoming gas is cooled from an initial temperature of about 95° F. to a temperature of about −205° F. and introduced into the methane recovery tower 114 through line 115 at a pressure of about 416 psia. An overhead stream composed of about 21.3% carbon monoxide, 48.8% hydrogen and 29.9% methane is taken off through line 116, passed through condenser 117 where it is cooled to a temperature of about −222° F., further cooled in condenser 118 to a temperature of about −224° F., cooled in condenser 119 to about −240° F., and discharged into reflux drum 120 at a pressure of about 410 psia. Liquid constituents from this drum are recycled as reflux to the top of the methane recovery tower through line 121. Gases from the reflux drum are passed through line 122 to exchanger 113 where they are heated to a temperature of about 90° F. at about 400 psia. This stream then passes through line 123 to the intake side of recycle gas compressor 124 where the gas is compressed to a pressure of about 575 psia at a temperature of 175° F. The resulting gas, containing about 21.0% carbon monoxide, about 68.8% hydrogen, and about 10.2% methane, serves as the recycle hydrogen and carbon monoxide for the process. This gas is withdrawn from the outlet of the recycle gas compressor through line 125. A portion of the stream is passed through line 126 to the molecular sieve regeneration furnace 109 and the rest is passed through line 127. Small amounts of gas used in the operation of the molecular sieve unit are withdrawn through line 128 and reinjected through lines 129 and 130 and the stream is then passed through line 131 to recycle gas preheat furnace 132. The recycle stream is heated to a temperature of about 450° F. at 550 psia, steam is added through line 75, additional steam is supplied through line 133, and the mixture of steam and recycle gas then passes through exchanger 51 to the primary coils of the preheat furnace. Here the mixture, introduced into the coils at a temperature of about 1150° F. and 540 psia, is heated to about 1450° F. at 520 psia. This hot mixture of steam and recycle gas then passes though line 134 to lines 40, 44 and 48 for introduction into the gasifier 41. The mixture will contain about 7.8% carbon monoxide, about 25.5% hydrogen, about 63.0% steam, and about 3.7% methane.

The methane recovery tower is operated using methane, ethylene and propylene as the refrigerants. In the refrigeration section of the unit, methane gas is fed from lines 135 and 136 to methane compressor 137 where the gas is compressed to a pressure of about 160 psia at about 89° F. The compressed gas then passes to the second stage 138 of this compressor where the pressure is raised to about 485 psia at 289° F. From here the methane flows through an aftercooler 139 and a precooler 140 where the temperature is reduced to about −35° F. The precooled gas then passes in part to methane condenser 141 and in part is circulated through line 142 to methane recovery tower reboiler 143. Liquid methane from the condenser then passes into methane accumulator 144 at a temperature of about −138° F. and a pressure of about 468 psia. Liquid methane flows from the accumulator through intermediate methane chiller 145 where it is cooled to −176° F. into methane interstage drum 146. Here the liquid methane is partially vaporized to produce a temperature of about −227° F. at about 45 psia. Methane from this storage drum is circulated through methane condenser 118 for cooling the overhead stream from the methane recovery tower. The overhead vapor from the drum passes through chiller 145 and is returned by means of line 136 to the methane compressor. Methane from the accumulator 144 also flows through line 147 and low pressure methane chiller 148 to methane drum 149 at a temperature of about −245° F. and a pressure of about 25 psia. Methane from the drum is circulated through condenser 119 and the vapor passes through chiller 148 and is returned through line 135 to the methane compressor. The methane circulated through the methane recovery tower reboiler 143 is returned through line 150 to the methane accumulator.

In the ethylene circuit of the refrigeration system, ethylene vapors are introduced through line 151 into the intake of ethylene compressor 152 at a pressure of about 20 psia. This vapor is compressed to about 245 psia at 180° F. and then passed through exchanger 153 where it is cooled to about 100° F. The cooled vapor is condensed in ethylene condenser 154 and then stored in ethylene accumulator 155 at about −35° F. and about 235 psia. From here the liquid ethylene flows to ethylene knockout drum 156 and is subsequently employed to chill the methane condenser 141. The ethylene vapor is then returned to the compressor by means of line 151.

In the propylene portion of the refrigeration circuit, propylene vapor is fed through line 157 to propylene compressor 158 at about 20 psia. The propylene is compressed to about 235 psia at a temperature of 198° F. and then cooled to about 100° F. in propylene condenser 159. Propylene is stored in propylene accumulator 160, passed to propylene knockout drum 161, and circulated to the knockout drum through the ethylene condenser to provide the necessary cooling. The vaporized propylene is returned from the knockout drum to the compressor through line 157. Separate propylene, ethylene and methane circuits are thus employed to provide the cooling necessary for operation of the methane recovery tower.

Liquid methane is withdrawn from the bottom of the methane recovery tower 114 through line 162 at a temperature of about −143° F. and a pressure of about 418 psia. A portion of this stream is circulated through the methane reboiler 143 through line 163 and returned to the tower. The remaining methane flows through line 164. Part of this stream passes through a pressure reduction valve not shown in the drawing and is chilled to a temperature of about −216° F. at 69 psia. This methane then passes through methane condenser 117 and the methane recovery tower feed-product exchanger 113 to drum 166 at about 90° F. and 61 psia. Vapor from the drum is fed through line 167 to methane booster compressor 168 where the pressure is raised to about 79 psia at 140° F. in the first stage. After flowing through aftercooler 169 where it is cooled to about 100° F., this stream flows into knockout drum 170.

A second portion of the liquid methane recovered from the bottom of tower 114 passes through lines 164 and line 171 containing a pressure reduction valve not shown in the drawing. This stream is chilled to a temperature of about −210° F. at 84 psia, passes through exchanger 113, and is fed through line 172 to knockout drum 170 at a temperature of about 90° F. The methane from drum 170 passes through line 173 to pipeline gas compressor 174 where it is compressed to about 277 psia at a temperature of about 356° F. After passing through innercooler 175, this gas flows through line 176 to the second stage 177 of the compressor where the pressure is raised to about 1025 psia at about 357° F. This gas is passed through product cooler 178 where it is cooled to about 120° F. at a pressure of 1015 psia and is then passed to the product methane pipeline. The gas thus recovered consists essentially of pure methane and contains only trace quantities of carbon monoxide.

In the system described above, hot char particles are continuously withdrawn from the gasifier in order to control the ash content of the system and permit the recovery of alkali metal constituents of the catalyst. In the operation shown in the drawing, these particles will typically contain about 19.6 weight percent carbon, about 0.2 weight percent hydrogen, about 0.3 weight percent oxygen, about 1.2 weight percent sulfur, about 32.3 weight percent ash, about 23.2 weight percent sodium carbonate and about 23.2 weight percent potassium carbonate. The particles are withdrawn at the gasification temperature of about 1300° F. and at about 500 psia and passed through withdrawal line 183 to char quench drum 184 where they are cooled to a temperature of about 700° F. by steam introduced through line 185 and water supplied through line 186. The resulting vapor, at a temperature of 700° F. and 500 psia, is passed through lines 187 and 53 to the high pressure steam generating section of the system. The solids then are fed through feeder 188 and line 189 to agitated char slurry drum 190. Here the solids are slurried in a rich alkali metal solution supplied through line 191 and this slurry, along with that produced in fines slurry drum 61, is then passed to the alkali metal recovery unit of the process through line 192.

The alkali metal recovery unit includes a battery of agitated mixing vessels 193, 194, 195, 196, 197, 198 and 199 operated at a temperature of about 230° F. and a pressure of about 30 psia. The slurry from line 192, containing solids from the char slurry drum and fines slurry drum and alkali metal solution recycled to the slurry drums from the alkali metal recovery unit as described hereafter, is introduced into hydroclone 200. Here a partial liquid-solids separation takes place. The liquid fraction from the slurry is taken overhead through line 201 to agitated alkali metal solution drum 202. From the drum, this solution is pumped through line 16 to the feed preparation unit. The solids fraction from hydroclone 200 is discharged into mixing vessel 193. Simultaneously alkali metal solution recovered from hydroclone 203 associated with vessel 195 is introduced into vessel 193 through line 204. The slurry level in vessel 193 is controlled by passing slurry through line 205 to heat exchanger 206 where the temperature is reduced from about 230° F. to about 120° F. Makeup water is added through line 207 and the diluted slurry is introduced through line 208 into mixing vessel 199. Slurry is drawn from the bottom of vessel 193 through line 209 and passed to hydroclone 210 associated with vessel 194. The liquid fraction recovered from the hydroclone passes through line 211. A portion of this liquid fraction is pumped through line 191 to the char slurry drum 190 and the remaining liquid is passed through line 212 to the fines slurry drum. This use of solution from the recovery unit in the slurry drum permits the extraction of significant quantities of soluble alkali metal constituents from the solids in the drums before they reach the alkali metal recovery unit. The solids from hydroclone 210 are discharged into mixing vessel 194 and at the same time liquid from hydroclone 213 is introduced through line 214. Slurry from vessel 194 is pumped through line 215 to hydroclone 203.

The slurry in vessel 195, containing solid from hydroclone 203 and liquid introduced from hydroclone 216 through line 217, passes through line 218 to vessel 196. Similarly, slurry from vessel 196, containing solids from hydroclone 219 and liquid recovered in hydroclone 213 and recycled through line 220, passes through line 221 to hydrocyclone 216. The solids recovered from this hydroclone, together with liquid recycled from hydroclone 222 through line 223 make up the slurry in vessel 197. Slurry is pumped from this vessel through line 224 to hydroclone 219. The solids recovered from this hydroclone, along with liquid recycled from hydroclone 225 through line 227, make up the slurry in vessel 198. This slurry is pumped to hydroclone 222 through line 226. The solids fraction which is withdrawn through line 228 will contain about 61 weight percent water, 13.9 weight percent char, 18.1 weight percent ash, 6.3 weight percent insoluble alkali metal catalyst constituents, and about 0.6 weight percent soluble alkali metal compounds from the catalyst. The liquids fraction recycled to the feed preparation step of the process through lines 201 and 16 will, in the particular installation shown, typically contain about 63.7 weight percent water, 34.3 weight percent of soluble sodium and potassium compounds recovered from the catalyst, 0.3 weight percent of suspended insoluble alkali metal catalyst constituents, 0.9 weight percent suspended ash particles, and 0.7 weight percent suspended char particles. It will be apparent from the foregoing that the alkali metal recovery unit involves a countercurrent liquid solid extraction system in which the solids withdrawn from the gasifier are contacted with a solution of dissolved alkali metal constituents in multiple stages and that this system permits substantially complete recovery of the soluble alkali metal constituents of the catalyst for reuse in the process.

The process of the invention has been described above in terms of the system presently considered the best mode for practicing the invention. It will be understood, however, that numerous modifications of the process specifically set forth can be made without departing from the invention. The feed preparation, gasification, gas purification, gas separation, and alkali metal recovery steps of the process can all be modified in various ways without loss of the advantages of the process over earlier gasification systems. In some instances, for example, it is advantageous to carry out the gasification step of the process in two or more stages in lieu of a single stage as shown. Similarly, other systems for cleaning up the raw product gas, removing acid gas constituents, separating methane from the recycle hydrogen and carbon monoxide, and recovering alkali metal constituents of the catalyst can be used. The particular system shown in the drawing is particularly effective, however, because it is characterized by high thermal efficiency, high carbon utilization, substantially complete recovery of soluble catalyst constituents, and the like.

The process of the invention is further illustrated by the results of gasification operations carried out with an Illinois coal similar to that referred to earlier. Finely divided particles of this coal were impregnated with an aqueous solution of potassium carbonate until an impregnated material containing 20 weight percent of the potassium carbonate salt was obtained. This material was dried at an elevated temperature of about 240° F. and then converted into char by passing the particles through a free-fall reactor containing a nitrogen atmosphere at atmospheric pressure and a temperature of 1550° F. The coal residence time in the reactor was about 1 second. This resulted in the formation of char particles containing the carbon-alkali metal catalyst. During this devolatilization of the char and formation of the catalyst, it was noted that the coal underwent considerably less swelling than normally occurs when the Illinois coal is devolatilized in the absence of the alkali metal compound. The yield of catalyst-containing char obtained in this initial step was 65%, based on the weight of total solids charged to the free-fall reactor. Much of the loss in weight was due to the evolution of volatile constituents and moisture from the solids as they were heated.

The catalyst-containing char prepared as described above was charged into a fixed bed reactor provided with facilities for the introduction of steam, hydrogen and carbon monoxide and the withdrawal of raw product gas. The bed had a bulk density of 24 pounds per cubic foot. The reactor was heated externally. A gas containing 75 volume percent hydrogen and 25 volume percent carbon monoxide was injected into the reactor at a pressure of 500 psig and a flow rate under standard conditions of 3.1 liters per hour. When the temperature of the bed reached 1330° F., steam was mixed with the input gas stream and injected into the reactor. The steam rate was equivalent to 5 cc of liquid water per hour.

The raw product gas from the reactor was passed through a condenser where it was cooled to room temperature and then to a pressure regulator where the pressure was reduced to a level slightly above atmospheric pressure. Following this, the gas was bubbled through an aqueous sodium hydroxide solution to remove carbon dioxide and then passed through a gas chromatograph for analysis. The analysis showed that the product gas contained 43 volume percent methane, 41 volume percent hydrogen, and 16 volume percent carbon monoxide. The rate under standard conditions was 5.4 liters per hour, corresponding to 2.3 liters per hour of methane and 3.1 liters per hour of a mixture of 75 volume percent hydrogen and 25 volume percent of carbon monoxide. It will be noted that the volume of hydrogen and carbon monoxide in the product gas was the same as the volume of hydrogen and carbon monoxide introduced into the reactor. There was thus no consumption of either hydrogen or carbon monoxide in the system. The overall reaction which took place was thus as follows:

$$2C + 2H_2O \rightarrow CH_4 + CO_2.$$

The steam conversion rate in the reaction was 70%.

Following the experimental run described above, an additional run was carried out using char containing a similar carbon-alkali metal catalyst and twice the steam and gas rates employed in the earlier run. The composition of the product gas obtained in this second run was similar to that obtained earlier but the methane content was slightly lower, about 40 volume percent instead of 43 volume percent as in the earlier run. Again it was found that there was no net consumption of either hydrogen or carbon monoxide, the sole overall reaction being that of steam with elemental carbon to produce methane and carbon dioxide. Increasing the steam rate thus increased the reaction rate but did not change the fundamental nature of the reaction. In the presence of the carbon-alkali metal catalyst, the gas phase reactions were in equilibrium.

Operations similar to those described above have been carried out on a continuous basis in a fluidized bed coal gasification pilot plant at a temperature of 1200° F. and a pressure of 100 psig. These tests have also demonstrated that the products of the process, ignoring contaminants due to sulfur and nitrogen compounds in the coal, consisted essentially of methane and carbon dioxide. The presence of equilibrium quantities of hydrogen and carbon monoxide to the gasifier suppresses reactions which produce large quantities of hydrogen and carbon monoxide in conventional gasification processes and permits the internal generation of heat not obtained to a significant extent in conventional processes.

It will be apparent from the foregoing that the invention provides an improved process for the production of methane which has pronounced advantageous over processes advocated in the past. Unlike conventional processes, it permits substantially hydrogen balanced, thermoneutral operations without the necessity for injecting large quantities of oxygen into the gasifier, employing a downstream water-gas shift reaction, and separately methanating the shifted gas thus produced. The process is significantly more effective from a technical and economical standpoint than earlier processes and in large part avoids the disadvantages which have characterized the processes suggested in the prior art.

We claim:

1. A process for the production of methane from a heavy oil or solid carbonaceous feed material and steam which comprises reacting said steam with said feed material to form essentially methane and carbon dioxide while suppressing the net formation of carbon monoxide and hydrogen in a reaction zone at a reaction temperature between about 1000° F. and about 1500° F. and at a reaction pressure in excess of about 100 psia, in the presence of a carbon-alkali metal catalyst comprising a carbon-alkali metal reaction product prepared by heating an intimate mixture of carbonaceous solids and an alkali metal constituent to an elevated temperature, said catalyst being present in a sufficient quantity to substantially equilibrate the gas phase reactions occuring during the reaction of said steam with said feed material, and in the presence of sufficient added equilibrium amounts, at said reaction temperature and pressure, of molecular hydrogen and carbon monoxide to provide substantially equilibrium quantities of hydrogen and carbon monoxide in said reaction zone at said reaction temperature and said reaction pressure, and withdrawing from said reaction zone a substantially equilibrium mixture, at said reaction temperature and pressure, of steam, molecular hydrogen, carbon monoxide, carbon dioxide, and methane, and recovering methane from the withdrawn mixture.

2. A process as defined by claim 1 wherein said feed material comprises coal and said carbon-alkali metal catalyst is prepared by treating said coal with an alkali metal compound and thereafter heating the treated coal to said reaction temperature in said reaction zone.

3. A process as defined by claim 1 wherein the withdrawn mixture is treated for the removal of carbon dioxide, methane is recovered from the treated gas, and hydrogen and carbon monoxide contained in said treated gas are recycled to said reaction zone as said added hydrogen and carbon monoxide.

4. A process as defined by claim 1 wherein said steam is reacted with said feed material in the substantial absence of added molecular oxygen.

5. A process as defined by claim 1 wherein said reaction temperature is between about 1200° F. and about 1400° F.

6. A process as defined by claim 1 wherein said reaction pressure is between about 300 and about 1500 psia.

7. A process as defined by claim 1 wherein said alkali metal constituent comprises potassium.

8. A process as defined by claim 1 including the additional steps of continuously withdrawing char particles from said reaction zone, slurrying the withdrawn char particles in an aqueous solution of an alkali metal compound, separating the slurry into a liquid fraction and a solids fraction, withdrawing said liquid fraction for the treatment of feed solids to said reaction zone, introducing said solids fraction into a multi-stage countercurrent extraction zone, and recovering from the solids in said extraction zone water-soluble alkali metal compounds.

9. A process as defined by claim 3 wherein said methane is recovered from said treated gas cryogenically, the refrigeration required for methane recovery being supplied in part by the vaporization of liquefied methane.

10. A process as defined by claim 3 wherein said hydrogen and said carbon monoxide contained in said treated gas are combined with steam, heated to said reaction temperature, and thereafter recycled to said reaction zone.

11. A process as defined by claim 3 wherein the withdrawn mixture is treated for the removal of carbon dioxide by scrubbing the gas with water, contacting the scrubbed gas with a solvent for acid gases, and thereafter passing the gas over a molecular sieve adsorbent.

12. A process for the production of methane which comprises reacting steam with carbonaceous solids to form essentially methane and carbon dioxide while suppressing the net formation of carbon monoxide and hydrogen in a reaction zone at a reaction temperature between about 1000° F. and about 1500° F. and at a reaction pressure in excess of about 100 psia, in the presence of a carbon-alkali metal catalyst comprising a carbon-alkali metal reaction product prepared by heating an intimate mixture of solid carbonaceous particles and an alkali metal constituent to an elevated temperature, said catalyst being present in a sufficient quantity to substantially equilibrate the gas phase reactions occuring during the reaction of said steam with said carbonaceous solids, and in the presence of sufficient added equilibrium amounts, at said reaction temperature and pressure of molecular hydrogen and carbon monoxide to provide substantially equilibrium concentrations of said molecular hydrogen and carbon monoxide in said reaction zone at said reaction temperature and pressure; withdrawing from said reaction zone raw product gas consisting essentially of an equilibrium mixture, at said reaction temperature and pressure, of methane, carbon dioxide, steam, molecular hydrogen, and carbon monoxide; treating said raw product gas for the removal of steam and carbon dioxide; recovering methane from the treated gas; and recycling hydrogen and carbon monoxide to said reaction zone for use as added hydrogen and carbon monoxide.

13. A process as defined by claim 12 wherein said carbonaceous solids comprise coal impregnated with potassium carbonate.

14. A process as defined by claim 12 wherein said reaction temperature is between about 1200° F. and about 1400° F. and said reaction pressure is between about 300 and about 1200 psia.

15. A process as defined by claim 12 wherein said carbon-alkali metal catalyst comprises a carbon-potassium reaction product.

16. A process for the production of methane and carbon dioxide from coal in the substantial absence of added molecular oxygen which comprises reacting steam with coal to form essentially methane and carbon dioxide while suppressing the net formation of carbon monoxide and hydrogen in a reaction zone at a reaction temperature between about 1000° F. and about 1500° F. and at a reaction pressure between about 300 psia and about 1500 psia, in the presence of a carbon alkali metal catalyst comprising a high temperature carbon-alkali metal reaction product prepared by heating an intimate mixture of carbonaceous solids and an alkali metal constituent to an elevated temperature, said catalyst being present in a sufficient quantity to substantially equilibrate the gas phase reactions occuring during the reaction of said steam with said coal, and in the presence of sufficient recycle hydrogen and carbon monoxide to provide substantially equilibrium concentrations of said recycle hydrogen and carbon monoxide in said reaction zone at said reaction temperature and pressure; withdrawing from said reaction zone an equilibrium mixture of methane, carbon dioxide, steam, molecular hydrogen, and carbon monoxide, said molecular hydrogen and carbon monoxide being present in said equilibrium mixture in quantities corresponding to the quantities of said recycle hydrogen and carbon monoxide added to said reaction zone; treating said equilibrium mixture for the removal of steam and carbon dioxide recovering methane from the treated gas; and recycling to said reaction zone the molecular hydrogen and carbon monoxide remaining following said separation of methane from said treated gas.

17. A process as defined by claim 16 wherein said coal is impregnated with an aqueous solution of a potassium compound and dried prior to the introduction of said coal into said reaction zone.

18. A process as defined by claim 17 wherein said aqueous solution comprises potassium compounds recovered from char withdrawn from said reaction zone.

19. A process as defined by claim 16 wherein said carbon-alkali metal catalyst comprises a high temperature carbon-sodium reaction product.

* * * * *